(12) United States Patent
Williams et al.

(10) Patent No.: US 10,085,744 B2
(45) Date of Patent: Oct. 2, 2018

(54) LOADING UNIT ATTACHMENT BAND FOR SURGICAL STAPLING INSTRUMENT

(71) Applicant: Covidien LP, Mansfield, MA (US)

(72) Inventors: Justin Williams, Southbury, CT (US); Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 459 days.

(21) Appl. No.: 14/804,814

(22) Filed: Jul. 21, 2015

(65) Prior Publication Data

US 2016/0157856 A1    Jun. 9, 2016

Related U.S. Application Data

(60) Provisional application No. 62/088,729, filed on Dec. 8, 2014.

(51) Int. Cl.
| | |
|---|---|
| *A61B 17/04* | (2006.01) |
| *A61B 17/10* | (2006.01) |
| *A61B 17/068* | (2006.01) |
| *A61B 17/115* | (2006.01) |
| *A61B 17/00* | (2006.01) |

(52) U.S. Cl.
CPC ........ *A61B 17/068* (2013.01); *A61B 17/1155* (2013.01); *A61B 2017/0046* (2013.01); *A61B 2017/00473* (2013.01); *A61B 2017/00477* (2013.01); *A61B 2017/00526* (2013.01)

(58) Field of Classification Search
CPC .............. A61B 17/068; A61B 17/1155; A61B 2017/00477
USPC ........................................... 227/175.1–182.1
See application file for complete search history.

(56) References Cited

U.S. PATENT DOCUMENTS

| | | | | |
|---|---|---|---|---|
| 2,110,397 | A | * | 3/1938 | Kangas ................. E21B 17/046 279/76 |
| 2,304,038 | A | * | 12/1942 | Thompson .......... B25B 23/0035 279/79 |
| 3,193,165 | A | | 7/1965 | Akhalaya et al. |
| 3,388,847 | A | | 6/1968 | Kasulin et al. |
| 3,552,626 | A | | 1/1971 | Astafiev et al. |
| 3,638,652 | A | | 2/1972 | Kelley |

(Continued)

FOREIGN PATENT DOCUMENTS

| | | |
|---|---|---|
| CA | 908529 A | 8/1972 |
| CN | 201481477 U | 5/2010 |

(Continued)

OTHER PUBLICATIONS

European Search Report dated May 10, 2016, issued in EP Application No. 15 19 8203.

(Continued)

*Primary Examiner* — Robert Long

(57) ABSTRACT

A loading unit and retention band assembly including a shell and a retention band. The shell has a proximal end portion that defines an engagement window and that includes an annular surface. The retention band is disposed radially about the annular surface of the proximal end portion and includes a resilient body having first and second ends. The first end includes a resilient lock that is configured to extend through the engagement window of the proximal end portion of the shell. The resilient lock is dimensioned to releasably engage a surgical instrument.

8 Claims, 6 Drawing Sheets

(56) References Cited

U.S. PATENT DOCUMENTS

| | | | |
|---|---|---|---|
| 3,753,582 A * | 8/1973 | Graham | F16L 37/088 |
| | | | 24/573.11 |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,647,241 A * | 3/1987 | Weber | F16B 7/0426 |
| | | | 403/18 |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,869,534 A * | 9/1989 | Ketcham | F16L 37/144 |
| | | | 285/24 |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,215,336 A * | 6/1993 | Worthing | F16L 19/005 |
| | | | 285/319 |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,275,443 A * | 1/1994 | Klinger | F16L 37/144 |
| | | | 285/305 |
| 5,282,810 A | 2/1994 | Allen et al. | |
| 5,285,944 A | 2/1994 | Green et al. | |
| 5,285,945 A | 2/1994 | Brinkerhoff et al. | |
| 5,291,910 A * | 3/1994 | Bui | A61H 3/02 |
| | | | 135/68 |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,405,175 A * | 4/1995 | Bonnah, II | F02M 55/004 |
| | | | 24/DIG. 53 |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,593,187 A * | 1/1997 | Okuda | F16L 37/088 |
| | | | 285/305 |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,772,159 A * | 6/1998 | Wendt | F16C 1/262 |
| | | | 248/27.1 |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| D425,784 S * | 5/2000 | Beugelsdyk | D8/395 |
| 6,056,070 A * | 5/2000 | Shinohara | B25D 9/145 |
| | | | 173/128 |
| 6,068,636 A | 5/2000 | Chen | |

(56) References Cited

U.S. PATENT DOCUMENTS

| | | | |
|---|---|---|---|
| 6,083,241 | A | 7/2000 | Longo et al. |
| 6,102,271 | A | 8/2000 | Longo et al. |
| 6,117,148 | A | 9/2000 | Ravo et al. |
| 6,119,913 | A | 9/2000 | Adams et al. |
| 6,126,058 | A | 10/2000 | Adams et al. |
| 6,142,933 | A | 11/2000 | Longo et al. |
| 6,149,667 | A | 11/2000 | Hovland et al. |
| 6,176,413 | B1 | 1/2001 | Heck et al. |
| 6,179,195 | B1 | 1/2001 | Adams et al. |
| 6,193,129 | B1 | 2/2001 | Bittner et al. |
| 6,203,553 | B1 | 3/2001 | Robertson et al. |
| 6,209,773 | B1 | 4/2001 | Bolduc et al. |
| 6,241,140 | B1 | 6/2001 | Adams et al. |
| 6,253,984 | B1 | 7/2001 | Heck et al. |
| 6,254,305 | B1 * | 7/2001 | Taylor ............... B25G 1/04 15/144.4 |
| 6,258,107 | B1 | 7/2001 | Balazs et al. |
| 6,264,086 | B1 | 7/2001 | McGuckin, Jr. |
| 6,269,997 | B1 | 8/2001 | Balazs et al. |
| 6,273,897 | B1 | 8/2001 | Dalessandro et al. |
| 6,279,809 | B1 | 8/2001 | Nicolo |
| 6,302,311 | B1 | 10/2001 | Adams et al. |
| 6,338,737 | B1 | 1/2002 | Toledano |
| 6,343,731 | B1 | 2/2002 | Adams et al. |
| 6,343,772 | B1 * | 2/2002 | Oi ..................... F16L 33/03 248/65 |
| 6,387,105 | B1 | 5/2002 | Gifford, III et al. |
| 6,398,795 | B1 | 6/2002 | McAlister et al. |
| 6,402,008 | B1 | 6/2002 | Lucas |
| 6,439,446 | B1 | 8/2002 | Perry et al. |
| 6,443,973 | B1 | 9/2002 | Whitman |
| 6,450,390 | B2 | 9/2002 | Heck et al. |
| 6,478,210 | B2 | 11/2002 | Adams et al. |
| 6,488,197 | B1 | 12/2002 | Whitman |
| 6,491,201 | B1 | 12/2002 | Whitman |
| 6,494,877 | B2 | 12/2002 | Odell et al. |
| 6,503,259 | B2 | 1/2003 | Huxel et al. |
| 6,517,566 | B1 | 2/2003 | Hovland et al. |
| 6,520,398 | B2 | 2/2003 | Nicolo |
| 6,533,157 | B1 | 3/2003 | Whitman |
| 6,539,920 | B1 * | 4/2003 | Spiers ................. F02M 55/004 123/456 |
| 6,551,334 | B2 | 4/2003 | Blatter et al. |
| 6,578,751 | B2 | 6/2003 | Hartwick |
| 6,585,144 | B2 | 7/2003 | Adams et al. |
| 6,588,643 | B2 | 7/2003 | Bolduc et al. |
| 6,592,596 | B1 | 7/2003 | Geitz |
| 6,601,749 | B2 | 8/2003 | Sullivan et al. |
| 6,605,078 | B2 | 8/2003 | Adams |
| 6,605,098 | B2 | 8/2003 | Nobis et al. |
| 6,612,622 | B2 * | 9/2003 | Andre ................. F16L 33/00 285/305 |
| 6,626,921 | B2 | 9/2003 | Blatter et al. |
| 6,629,630 | B2 | 10/2003 | Adams |
| 6,631,837 | B1 | 10/2003 | Heck |
| 6,632,227 | B2 | 10/2003 | Adams |
| 6,632,237 | B2 | 10/2003 | Ben-David et al. |
| 6,652,542 | B2 | 11/2003 | Blatter et al. |
| 6,659,327 | B2 | 12/2003 | Heck et al. |
| 6,676,671 | B2 | 1/2004 | Robertson et al. |
| 6,681,979 | B2 | 1/2004 | Whitman |
| 6,685,079 | B2 | 2/2004 | Sharma et al. |
| 6,695,198 | B2 | 2/2004 | Adams et al. |
| 6,695,199 | B2 | 2/2004 | Whitman |
| 6,698,643 | B2 | 3/2004 | Whitman |
| 6,716,222 | B2 | 4/2004 | McAlister et al. |
| 6,716,233 | B1 | 4/2004 | Whitman |
| 6,726,697 | B2 | 4/2004 | Nicholas et al. |
| 6,736,031 | B1 * | 5/2004 | Kang ................... B25B 7/12 81/322 |
| 6,742,692 | B2 | 6/2004 | Hartwick |
| 6,743,244 | B2 | 6/2004 | Blatter et al. |
| 6,763,993 | B2 | 7/2004 | Bolduc et al. |
| 6,769,590 | B2 | 8/2004 | Vresh et al. |
| 6,769,594 | B2 | 8/2004 | Orban, III |
| 6,820,791 | B2 | 11/2004 | Adams |
| 6,821,282 | B2 | 11/2004 | Perry et al. |
| 6,827,246 | B2 | 12/2004 | Sullivan et al. |
| 6,840,423 | B2 | 1/2005 | Adams et al. |
| 6,843,403 | B2 | 1/2005 | Whitman |
| 6,846,308 | B2 | 1/2005 | Whitman et al. |
| 6,852,122 | B2 | 2/2005 | Rush |
| 6,866,178 | B2 | 3/2005 | Adams et al. |
| 6,872,214 | B2 | 3/2005 | Sonnenschein et al. |
| 6,874,669 | B2 | 4/2005 | Adams et al. |
| 6,884,250 | B2 | 4/2005 | Monassevitch et al. |
| 6,905,504 | B1 | 6/2005 | Vargas |
| 6,938,814 | B2 | 9/2005 | Sharma et al. |
| 6,942,675 | B1 | 9/2005 | Vargas |
| 6,945,444 | B2 | 9/2005 | Gresham et al. |
| 6,953,138 | B1 | 10/2005 | Dworak et al. |
| 6,957,758 | B2 | 10/2005 | Aranyi |
| 6,959,851 | B2 | 11/2005 | Heinrich |
| 6,978,922 | B2 | 12/2005 | Bilotti et al. |
| 6,981,941 | B2 | 1/2006 | Whitman et al. |
| 6,981,979 | B2 | 1/2006 | Nicolo |
| 6,983,958 | B2 * | 1/2006 | Rautureau ............ F16L 37/088 285/305 |
| 7,032,798 | B2 | 4/2006 | Whitman et al. |
| 7,059,331 | B2 | 6/2006 | Adams et al. |
| 7,059,510 | B2 | 6/2006 | Orban, III |
| 7,077,856 | B2 | 7/2006 | Whitman |
| 7,080,769 | B2 | 7/2006 | Vresh et al. |
| 7,086,267 | B2 | 8/2006 | Dworak et al. |
| 7,114,642 | B2 | 10/2006 | Whitman |
| 7,118,528 | B1 | 10/2006 | Piskun |
| 7,122,044 | B2 | 10/2006 | Bolduc et al. |
| 7,128,748 | B2 | 10/2006 | Mooradian et al. |
| 7,141,055 | B2 | 11/2006 | Abrams et al. |
| 7,168,604 | B2 | 1/2007 | Milliman et al. |
| 7,179,267 | B2 | 2/2007 | Nolan et al. |
| 7,182,239 | B1 | 2/2007 | Myers |
| 7,195,142 | B2 | 3/2007 | Orban, III |
| 7,207,168 | B2 | 4/2007 | Doepker et al. |
| 7,220,237 | B2 | 5/2007 | Gannoe et al. |
| 7,234,624 | B2 | 6/2007 | Gresham et al. |
| 7,235,089 | B1 | 6/2007 | McGuckin, Jr. |
| RE39,841 | E | 9/2007 | Bilotti et al. |
| 7,285,125 | B2 | 10/2007 | Viola |
| 7,303,106 | B2 | 12/2007 | Milliman et al. |
| 7,303,107 | B2 | 12/2007 | Milliman et al. |
| 7,309,341 | B2 | 12/2007 | Ortiz et al. |
| 7,322,994 | B2 | 1/2008 | Nicholas et al. |
| 7,325,713 | B2 | 2/2008 | Aranyi |
| 7,334,718 | B2 | 2/2008 | McAlister et al. |
| 7,335,212 | B2 | 2/2008 | Edoga et al. |
| 7,347,454 | B2 * | 3/2008 | Martus ................ F16L 33/03 24/20 R |
| 7,364,060 | B2 | 4/2008 | Milliman |
| 7,398,908 | B2 | 7/2008 | Holsten et al. |
| 7,399,305 | B2 | 7/2008 | Csiky et al. |
| 7,401,721 | B2 | 7/2008 | Holsten et al. |
| 7,401,722 | B2 | 7/2008 | Hur |
| 7,407,075 | B2 | 8/2008 | Holsten et al. |
| 7,410,086 | B2 | 8/2008 | Ortiz et al. |
| 7,422,137 | B2 | 9/2008 | Manzo |
| 7,422,138 | B2 | 9/2008 | Bilotti et al. |
| 7,431,191 | B2 | 10/2008 | Milliman |
| 7,438,718 | B2 | 10/2008 | Milliman et al. |
| 7,455,676 | B2 | 11/2008 | Holsten et al. |
| 7,455,682 | B2 | 11/2008 | Viola |
| 7,481,347 | B2 | 1/2009 | Roy |
| 7,494,038 | B2 | 2/2009 | Milliman |
| 7,506,791 | B2 | 3/2009 | Omaits et al. |
| 7,516,877 | B2 | 4/2009 | Aranyi |
| 7,527,185 | B2 | 5/2009 | Harari et al. |
| 7,537,602 | B2 | 5/2009 | Whitman |
| 7,546,939 | B2 | 6/2009 | Adams et al. |
| 7,546,940 | B2 | 6/2009 | Milliman et al. |
| 7,547,312 | B2 | 6/2009 | Bauman et al. |
| 7,556,186 | B2 | 7/2009 | Milliman |
| 7,559,451 | B2 | 7/2009 | Sharma et al. |
| 7,585,306 | B2 | 9/2009 | Abbott et al. |

(56) References Cited

U.S. PATENT DOCUMENTS

| | | |
|---|---|---|
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,748,645 B2 * | 7/2010 | Breese ............... A01M 7/005 180/315 |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,891,343 B2 * | 2/2011 | Braun ............... F02M 55/002 123/446 |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,220,840 B2 * | 7/2012 | Garraffa ............... B63C 11/205 128/201.27 |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,397,972 B2 * | 3/2013 | Kostrzewski .... A61B 17/07207 227/175.2 |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,875,972 B2 * | 11/2014 | Weisenburgh, II ........................ A61B 17/07207 227/175.1 |
| 8,899,466 B2 * | 12/2014 | Baxter, III ............ A61B 17/115 227/179.1 |
| 9,009,927 B2 * | 4/2015 | Rigollet ............... F16L 33/03 24/270 |
| 9,113,885 B2 * | 8/2015 | Hodgkinson ......... A61B 17/1114 |
| 9,168,042 B2 * | 10/2015 | Milliman ............ A61B 17/1155 |

(56) References Cited

U.S. PATENT DOCUMENTS

| | | | |
|---|---|---|---|
| 9,364,230 B2* | 6/2016 | Shelton, IV | A61B 17/07207 |
| 9,504,470 B2* | 11/2016 | Milliman | A61B 17/07292 |
| 9,506,592 B2* | 11/2016 | Turnau, III | F16L 37/0915 |
| 9,739,403 B2* | 8/2017 | Freter | F16L 37/0841 |
| 9,757,133 B2* | 9/2017 | Latimer | A61B 17/1155 |
| 9,845,907 B2* | 12/2017 | Hess | F16L 23/04 |
| 2003/0111507 A1 | 6/2003 | Nunez | |
| 2004/0059227 A1 | 3/2004 | Nita et al. | |
| 2004/0194324 A1 | 10/2004 | Youn-Chyuan | |
| 2005/0051597 A1 | 3/2005 | Toledano | |
| 2005/0085830 A1* | 4/2005 | Lehman | A61B 17/1285 606/143 |
| 2005/0099001 A1* | 5/2005 | Cassel | F01N 13/1805 285/23 |
| 2005/0107813 A1 | 5/2005 | Gilete Garcia | |
| 2005/0192601 A1* | 9/2005 | Demarais | A61B 17/0401 606/151 |
| 2005/0236459 A1* | 10/2005 | Gresham | A61B 17/068 227/175.1 |
| 2006/0000869 A1 | 1/2006 | Fontayne | |
| 2006/0011698 A1 | 1/2006 | Okada et al. | |
| 2006/0201989 A1 | 9/2006 | Ojeda | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2007/0176416 A1* | 8/2007 | Swank | F01N 13/1816 285/226 |
| 2008/0179375 A1 | 7/2008 | Scirica | |
| 2008/0281299 A1* | 11/2008 | Menn | A61B 1/0014 606/1 |
| 2008/0308605 A1 | 12/2008 | Scirica | |
| 2009/0078336 A1* | 3/2009 | Baudoux | B60K 15/04 141/311 R |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2009/0326540 A1 | 12/2009 | Estes | |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0093205 A1* | 4/2010 | Stone | H01R 13/5219 439/352 |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0253065 A1* | 10/2010 | Lotti | F16L 33/227 285/3 |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0013796 A1* | 1/2011 | Agustiar | H04R 25/604 381/324 |
| 2011/0095070 A1* | 4/2011 | Patel | A61B 17/115 227/181.1 |
| 2011/0114697 A1 | 5/2011 | Baxter, III et al. | |
| 2011/0114700 A1 | 5/2011 | Baxter, III et al. | |
| 2011/0132964 A1* | 6/2011 | Weisenburgh, II | A61B 17/07207 227/176.1 |
| 2011/0142529 A1* | 6/2011 | Oh | A46B 7/04 401/268 |
| 2011/0144640 A1 | 6/2011 | Heinrich et al. | |
| 2011/0147432 A1 | 6/2011 | Heinrich et al. | |
| 2011/0186614 A1 | 8/2011 | Kasvikis | |
| 2011/0192882 A1 | 8/2011 | Hess et al. | |
| 2011/0205072 A1* | 8/2011 | Ben-Mansour | G01M 3/183 340/605 |
| 2011/0276036 A1 | 11/2011 | Spranger et al. | |
| 2012/0061448 A1 | 3/2012 | Zingman | |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0056516 A1 | 3/2013 | Viola | |
| 2013/0060258 A1 | 3/2013 | Giacomantonio | |
| 2013/0096591 A1 | 4/2013 | Hart et al. | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0123705 A1 | 5/2013 | Holm et al. | |
| 2013/0126580 A1 | 5/2013 | Smith et al. | |
| 2013/0153630 A1 | 6/2013 | Miller et al. | |
| 2013/0153631 A1 | 6/2013 | Vasudevan et al. | |
| 2013/0153633 A1 | 6/2013 | Casasanta, Jr. et al. | |
| 2013/0153634 A1 | 6/2013 | Carter et al. | |
| 2013/0153638 A1 | 6/2013 | Carter et al. | |
| 2013/0153639 A1 | 6/2013 | Hodgkinson et al. | |
| 2013/0158566 A1* | 6/2013 | Harris | A61B 17/1285 606/142 |
| 2013/0167365 A1* | 7/2013 | Herren | F16L 1/06 29/700 |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181029 A1 | 7/2013 | Milliman | |
| 2013/0181035 A1 | 7/2013 | Milliman | |
| 2013/0181036 A1 | 7/2013 | Olson et al. | |
| 2013/0186930 A1 | 7/2013 | Wenchell et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193191 A1 | 8/2013 | Stevenson et al. | |
| 2013/0193192 A1 | 8/2013 | Casasanta, Jr. et al. | |
| 2013/0200131 A1 | 8/2013 | Racenet et al. | |
| 2013/0200607 A1* | 8/2013 | Rodenberg | F16L 37/0915 285/82 |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0277411 A1 | 10/2013 | Hodgkinson et al. | |
| 2013/0277412 A1 | 10/2013 | Gresham et al. | |
| 2013/0284792 A1 | 10/2013 | Ma | |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306701 A1 | 11/2013 | Olson | |
| 2013/0306707 A1 | 11/2013 | Viola et al. | |
| 2014/0001236 A1* | 1/2014 | Shelton, IV | A61B 17/07207 227/176.1 |
| 2014/0008413 A1 | 1/2014 | Williams | |
| 2014/0012317 A1 | 1/2014 | Orban et al. | |
| 2014/0025071 A1* | 1/2014 | Sims | A61B 18/1445 606/46 |
| 2014/0116832 A1* | 5/2014 | Beiser | F16D 41/14 192/54.1 |
| 2014/0217148 A1* | 8/2014 | Penna | A61B 17/07292 227/179.1 |
| 2014/0309677 A1 | 10/2014 | Baldwin | |
| 2014/0312095 A1* | 10/2014 | Scirica | A61B 17/07207 227/176.1 |
| 2014/0373652 A1* | 12/2014 | Zergiebel | F16H 19/02 74/89.23 |
| 2015/0108201 A1 | 4/2015 | Williams | |
| 2015/0320420 A1 | 11/2015 | Penna et al. | |
| 2016/0157856 A1* | 6/2016 | Williams | A61B 17/068 227/175.1 |
| 2016/0175026 A1* | 6/2016 | Bhagat | A61B 18/1445 606/52 |

(56) References Cited

U.S. PATENT DOCUMENTS

| | | | | |
|---|---|---|---|---|
| 2016/0192934 A1* | 7/2016 | Williams | | A61B 17/105 |
| | | | | 227/176.1 |
| 2016/0192938 A1* | 7/2016 | Sgroi, Jr. | | A61B 17/1155 |
| | | | | 227/175.1 |
| 2016/0245443 A1* | 8/2016 | Zonneveld | | F16L 37/18 |
| 2016/0279279 A1* | 9/2016 | Wonnacott | | A61L 9/048 |
| 2017/0079660 A1* | 3/2017 | Sgroi | | A61B 17/068 |
| 2017/0198887 A1* | 7/2017 | Veloskey | | F21V 17/02 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1190796 A1 | 3/2002 |
| EP | 1354560 A2 | 10/2003 |
| EP | 1631199 A1 | 3/2006 |
| EP | 2090245 A1 | 8/2009 |
| EP | 2524656 A2 | 11/2012 |
| EP | 2774549 A2 | 9/2014 |
| EP | 3042619 A1 | 7/2016 |
| FR | 1136020 A | 5/1957 |
| FR | 1461464 A | 2/1966 |
| FR | 1588250 A | 4/1970 |
| FR | 2243758 A1 | 4/1975 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9805261 A2 | 2/1998 |
| WO | 2001/054594 A1 | 8/2001 |
| WO | 2004107990 A1 | 12/2004 |
| WO | 2008/107918 A1 | 9/2008 |
| WO | 2012015917 A1 | 2/2012 |
| WO | 2014139327 A1 | 9/2014 |
| WO | 2014139440 A1 | 9/2014 |
| WO | 2014139442 A1 | 9/2014 |
| WO | 2014139467 A1 | 9/2014 |
| WO | 20140139442 A1 | 9/2014 |

OTHER PUBLICATIONS

European Search Report dated Sep. 1, 2016, issued in EP 16166326.
Partial European Search Report dated Jan. 16, 2017, issued in EP Appln. No. 16180339.
European Search Report dated Nov. 30, 2016, issued in EP Application No. 16181395.
EP Examination Report dated Jun. 20, 2017, issued in EP Application No. 16150288.
European Search Report dated May 23, 2017, issued in EP Application No. 16189648.
U.S. Appl. No. 14/591,193, filed Jan. 7, 2015, inventor: Sgroi, Jr.
U.S. Appl. No. 14/810,811, filed Jul. 28, 2015, inventor: Sgroi, Jr., et al.
U.S. Appl. No. 14/805,547, filed Jul. 22, 2015, inventor: Scirica, et al.
U.S. Appl. No. 14/859,590, filed Sep. 21, 2015, inventor: Sgroi.
U.S. Appl. No. 62/100,512, filed Jan. 7, 2015, inventor: Williams et al.
U.S. Appl. No. 62/150,913, filed Apr. 22, 2015, inventor: Penna et al.
European Search Report dated May 17, 2016, issued in EP Application No. 16150284.
European Search Report dated Jun. 24, 2016, issued in EP Application No. 16150288.5.

* cited by examiner

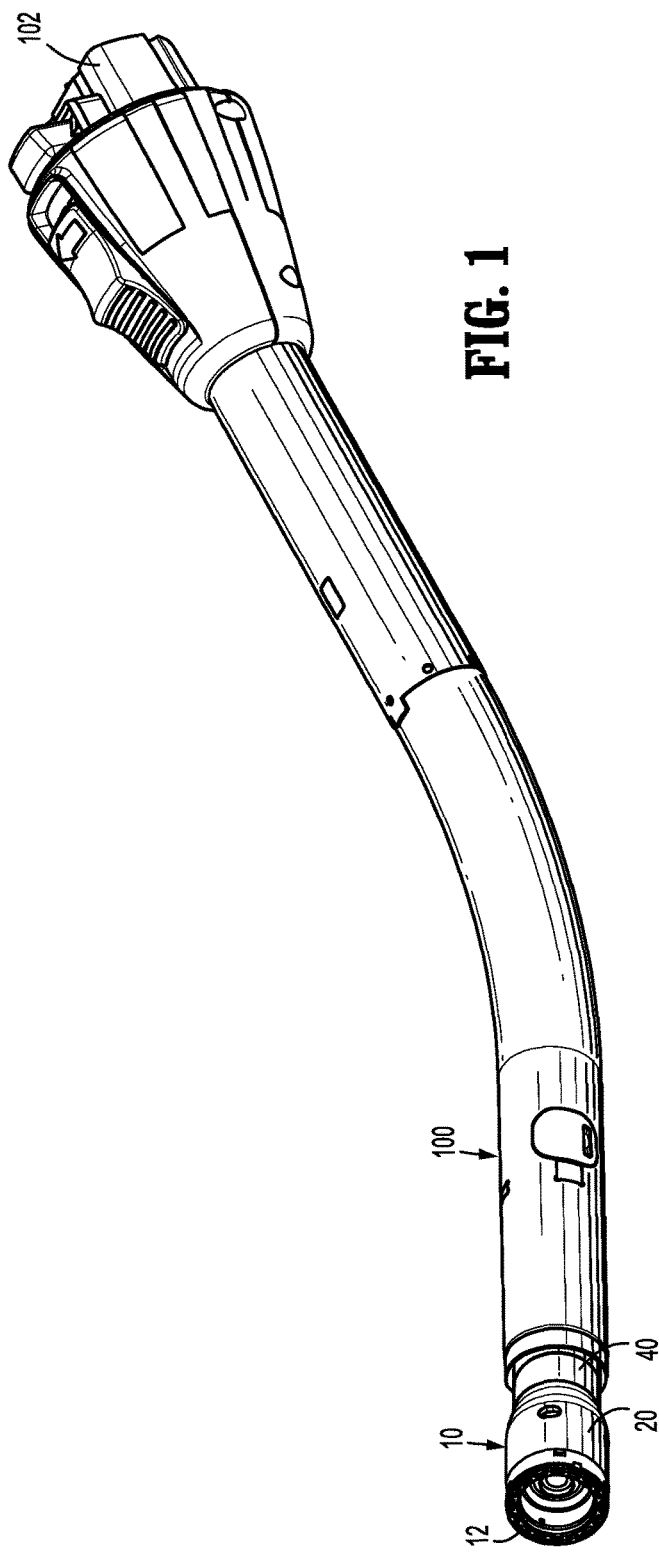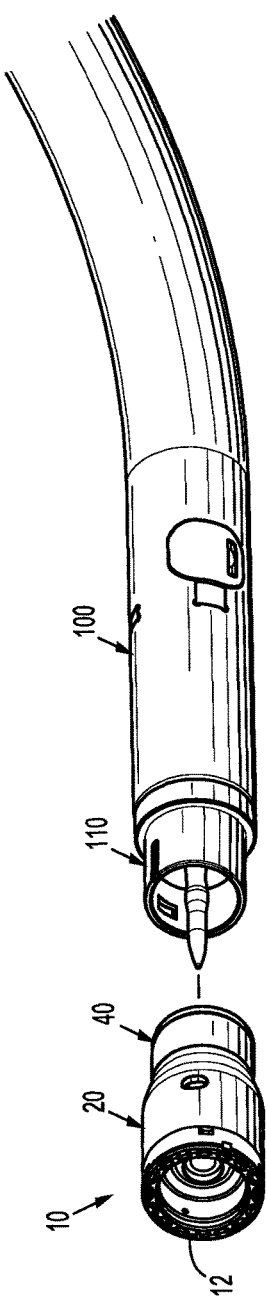

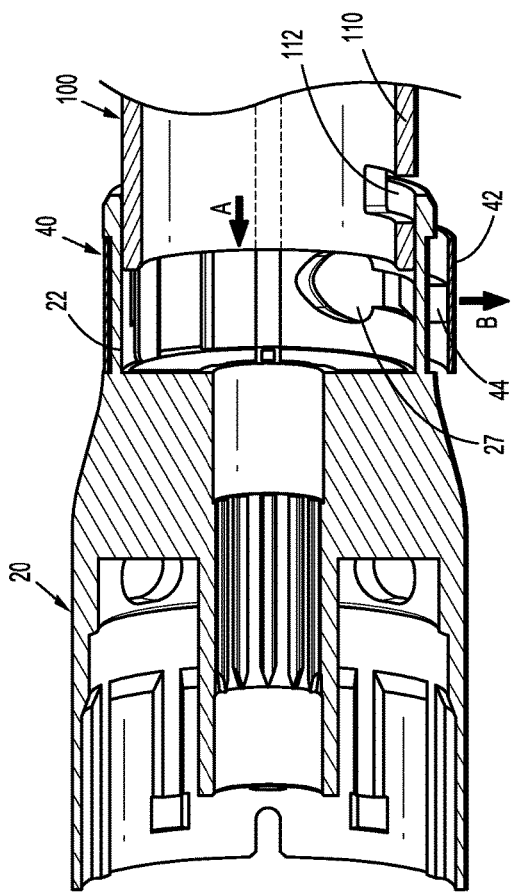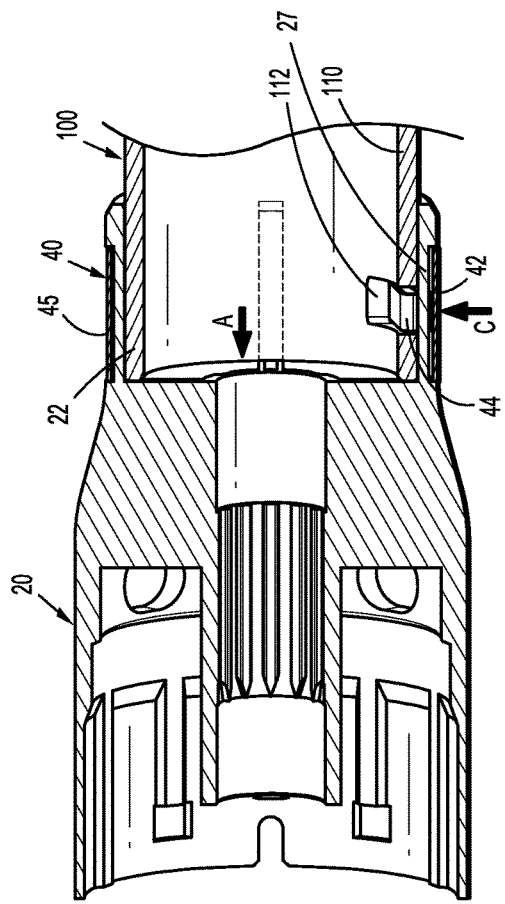

LOADING UNIT ATTACHMENT BAND FOR SURGICAL STAPLING INSTRUMENT

CROSS-REFERENCE TO RELATED APPLICATIONS

This application claims the benefit of and priority to U.S. Provisional Patent Application No. 62/088,729, filed Dec. 8, 2014, the entire disclosure of which is incorporated by reference herein.

BACKGROUND

1. Technical Field

The present disclosure relates generally to surgical stapling instruments. More specifically, the present disclosure relates to circular stapling instruments having replaceable loading units.

2. Background of Related Art

Surgical stapling instruments configured to join tissue portions during a surgical procedure are well known. These instruments include linear end effectors which are oriented parallel or transverse to a longitudinal axis of the instrument. These instruments also include circular end effectors. Typically, the linear stapling instruments include a disposable loading unit or a replaceable cartridge that allows the stapling instrument to be used multiple times. In contrast, conventional circular stapling instruments typically include a cartridge or shell assembly that is fixedly attached to the instrument such that the instrument must be disposed of after a single use.

A need exists in the art for a simple, inexpensive instrument for releasably, but securely, fastening a cartridge or shell assembly to a circular stapling instrument to facilitate reuse of the stapling instrument.

SUMMARY

In an aspect of the present disclosure, a loading unit and retention band assembly including a shell and a retention band. The shell has a proximal end portion that defines an engagement window and that includes an annular surface. The retention band is disposed radially about the annular surface of the proximal end portion and includes a resilient body having first and second ends. The first end includes a resilient lock that is configured to extend through the engagement window of the proximal end portion of the shell. The resilient lock is dimensioned to releasably engage a surgical instrument.

In aspects, the shell includes a distal end portion that supports a staple cartridge. The annular surface may define an annular groove and the body of the retention band may be disposed within the annular groove.

In some aspects, the resilient lock of the retention band may extend through the engagement window towards a longitudinal axis of the shell. The proximal end portion of the shell may define a clip opening that is radially offset from the engagement window. The second end of the retention band may include a clip that extends through the clip opening and captures a portion of the proximal end portion of the shell between the clip and the body of the retention band. The proximal end portion of the shell may define a tab opening. The clip opening may be positioned between the engagement window and the tab opening. The retention band may include a tab adjacent the second end of the body that extends from the body towards the clip. The tab may extend through the tab opening to fix the second end of the retention band relative to the proximal end portion. The resilient body of the retention band may be configured to urge the first and second ends towards one another.

In another aspect of the present disclosure, a surgical instrument and loading unit assembly includes a loading unit, a surgical instrument, and a retention band. The loading unit includes a shell that has a proximal end portion that includes an annular surface and that defines an engagement window. The surgical instrument has a distal end that is received within the proximal end portion of the shell. The retention band is disposed radially about the annular surface of the proximal end portion. The retention band has a resilient body that includes first and second ends. The first end includes a resilient lock that extends through the engagement window of the proximal end portion of the shell to releasably couple the loading unit to the surgical instrument.

In aspects, the distal end of the surgical instrument defines an attachment window. The resilient lock of the retention band may extend through the engagement and attachment windows to releasably couple the loading unit to the surgical instrument. The shell may define a longitudinal axis and the proximal end portion of the shell may include a key that protrudes inward from the proximal end portion. The distal end of the surgical instrument defines a keyway which receives the key to radially fix the loading unit and the surgical instrument relative to one another. The key may be positioned about the proximal end portion of the loading unit and the keyway may be positioned about the distal end of the surgical instrument to radially align the engagement window of the loading unit with the attachment window of the surgical instrument.

In another aspect of the present disclosure, a method of securing a loading unit to a surgical instrument includes inserting a distal end of the surgical instrument into a proximal end portion of the loading unit, deforming a retention band that is disposed on the proximal end portion of the loading unit to allow the loading unit to fully receive the distal end of the surgical instrument, and releasing the retention band when the distal end of the surgical instrument is fully received within the proximal end portion of the loading unit to secure the loading unit to the surgical instrument.

In aspects, the method includes attaching the retention band to the proximal end portion of the loading unit. Attaching the retention band to the proximal end portion of the loading unit may precede inserting a distal end of the surgical instrument into the proximal end portion of the loading unit.

In some aspects, attaching the retention band to the proximal end portion of the loading unit includes securing a second end of the retention band to the proximal end portion of the loading unit and positioning a body of the retention band within an annular groove defined in the proximal end portion of the loading unit. The body of the retention band may be positioned between the first and second ends of the retention band. Securing the second end of the retention band to the proximal end portion of the loading unit may include capturing a portion of the proximal end portion between a clip extending from the second end of the retention band and the body of the retention band. Capturing the portion of the proximal end portion may include rotating the retention band in a first direction until a tab adjacent the second end of the retention band that is disposed within a tab opening defined in the proximal end portion. The tab may engage the tab opening to prevent the retention band from rotating in a second direction opposite the first direction.

In particular aspects, positioning the body of the retention band within the annular groove includes positioning a lock of the retention band through an engagement window formed in the proximal end portion of the loading unit after positioning the body of the retention band. Positioning the lock of the retention band through the engagement window may include a radiating portion of the lock engaging an end surface of the engagement window that is spaced apart from the first end of the retention band to prevent the retention band from rotating in the second direction.

In certain aspects, the method includes separating the loading unit from the surgical instrument after releasing the first end of the retention band. Separating the loading unit from the adapter may include deforming the retention band to permit the distal end of the surgical instrument to release the proximal end portion of the loading unit and withdrawing the distal end of the surgical instrument from within the proximal end portion of the loading unit.

In aspects, inserting the distal end of the surgical instrument into the proximal end portion of the loading unit includes the distal end abutting a lock of the retention band that extends through an engagement window of the proximal end portion. Deforming the first end of the retention band may include removing the lock from the engagement window. Releasing the first end of the retention band when the distal end of the surgical instrument is fully received within the proximal end portion of the loading unit may include the lock of the retention band that extends through the engagement window that is formed in the proximal end portion of the shell. The attachment window may be formed in the distal end of the surgical instrument to secure the loading unit to the surgical instrument.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 1 is a perspective view of a circular stapling surgical instrument in accordance with the present disclosure with a loading unit releasably coupled to a distal end of the surgical instrument;

FIG. 2 is a perspective view of the adapter of FIG. 1 with the loading unit decoupled from the surgical instrument;

FIG. 11 is a side cross-sectional view with of the loading unit and surgical instrument of FIG. 10 with a portion of the retention band deformed; and FIG. 12 is a side cross-sectional view of the loading unit and the surgical instrument of FIG. 11 coupled together.

DETAILED DESCRIPTION OF EMBODIMENTS

Figure 3:
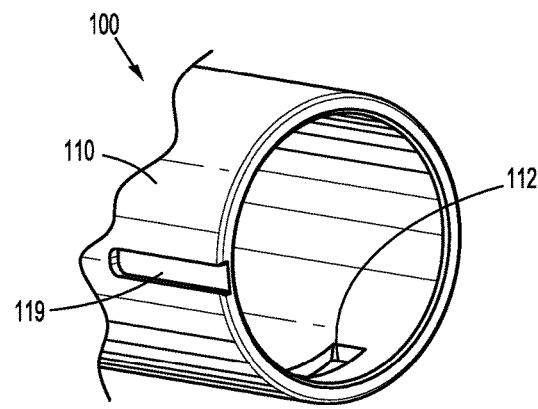
FIG. 3 is an enlarged perspective view of a portion of the distal end of the surgical instrument of FIG. 2.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the instrument or component thereof that is closest to the clinician and the term "distal" refers to the portion of the instrument or component thereof that is farthest from the clinician.

FIGS. 1 and 2 illustrate a loading unit 10 and an adapter 100 in accordance with an embodiment of the present disclosure. The loading unit 10 is configured for selective connection to a powered hand held electromechanical instrument (not shown) via the adapter 100. Alternatively, the loading unit 10 can be configured for connection to a manually actuated handle assembly or stapling instrument such as described in U.S. Pat. No. 8,789,737 ("the '737 Patent"), which is incorporated herein by reference. In such an embodiment, an elongated body portion of the stapling instrument may have a configuration similar to that of the adapter 100 as shown in FIG. 2. In the illustrated embodiment, the loading unit 10 is releasably coupled to a distal end portion 110 of the adapter 100 and includes a staple cartridge 12, a shell assembly 20, and an attachment member or retention band 40 for releasably securing the loading unit 10 to the adapter 100. The loading unit 10 may also include an anvil (not shown). The adapter 100 is configured to translate movement of a stapling instrument, e.g., an electromechanical instrument (not shown), to actuate the staple cartridge 12 to suture and cut tissue (not shown). A proximal end 102 of the adapter 100 is attachable to the stapling instrument to actuate the staple cartridge 12. It is contemplated that the proximal end 102 of the adapter 100 may be attached to a manually actuated instrument such as described in the '737 Patent to actuate the staple cartridge 12.

For a detailed description of the structure and function of an exemplary adapter and loading unit, please refer to commonly owned U.S. Provisional Patent Application Ser. No. 62/066,518, filed on Oct. 21, 2014. For a detailed description of the structure and function of an exemplary electromechanical instrument, please refer to commonly owned U.S. patent application Ser. No. 13/484,975, filed on May 31, 2012, now published as U.S. Patent Publication No. 2012/0253329. Each of these applications is incorporated herein by reference in its entirety.

With reference to FIG. 3, the distal end 110 of the adapter 100 defines an attachment window 112 and a keyway 119. The attachment window 112 extends through the adapter 100 and is configured to interact with the retention band 40 to longitudinally fix the shell assembly 20 to the distal end 110 of the adapter 100 as detailed below. The keyway 119 is defined in the outer surface of the distal end 110 of the adapter 100 and extends parallel to a longitudinal axis of the adapter 100. The keyway 119 is sized and configured to radially align and fix the shell assembly 20 to the adapter 100 as detailed below. As shown, the keyway 119 does not pass entirely through the distal end 110 of the adapter 100;

however, it is contemplated that the keyway 119 may pass entirely through the distal end 110 of the adapter 100 to form a longitudinal slot in the distal end 110 of the adapter 100.

Figure 4:
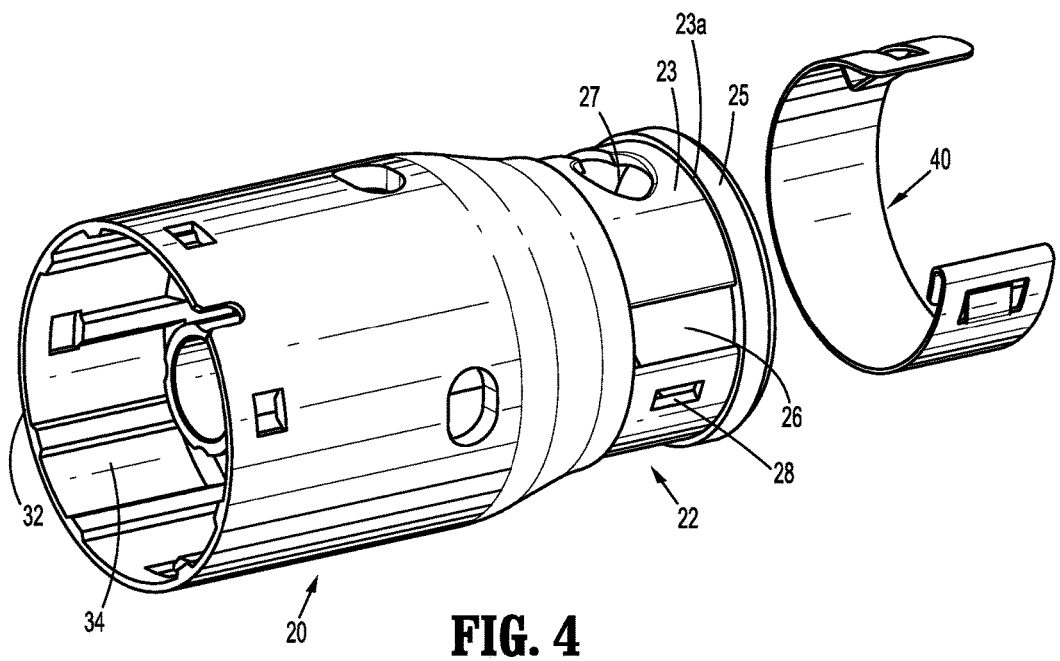
FIG. 4 is a perspective view of the loading unit of FIG. 2 with a retention band separated from the shell assembly.
Figure 5:
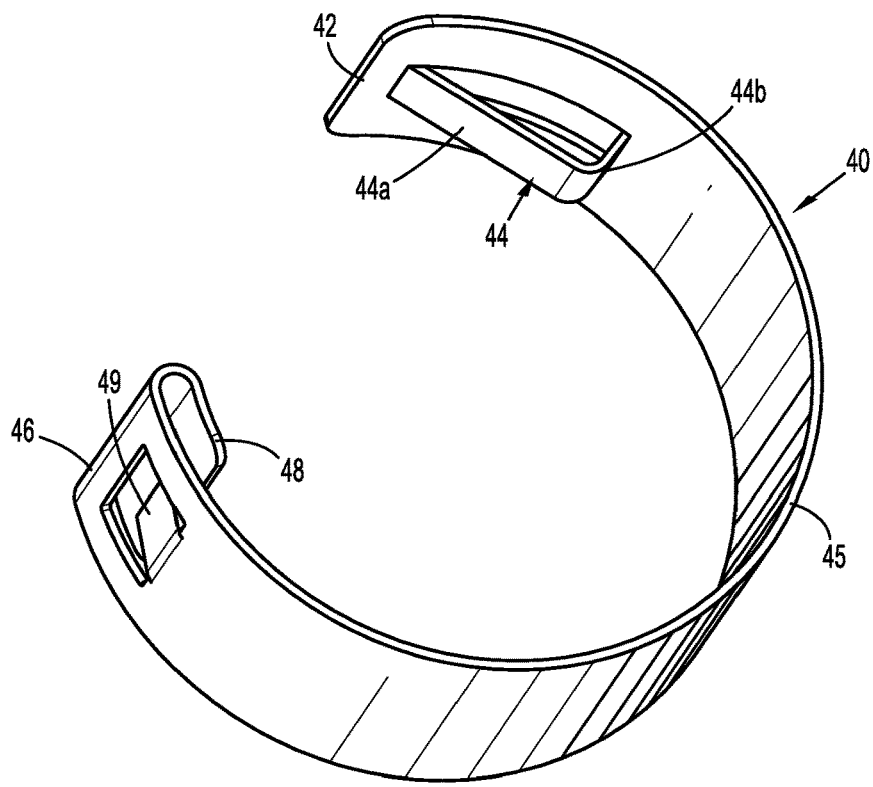
FIG. 5 is a perspective view of the retention band of FIG. 4.
Figure 6:
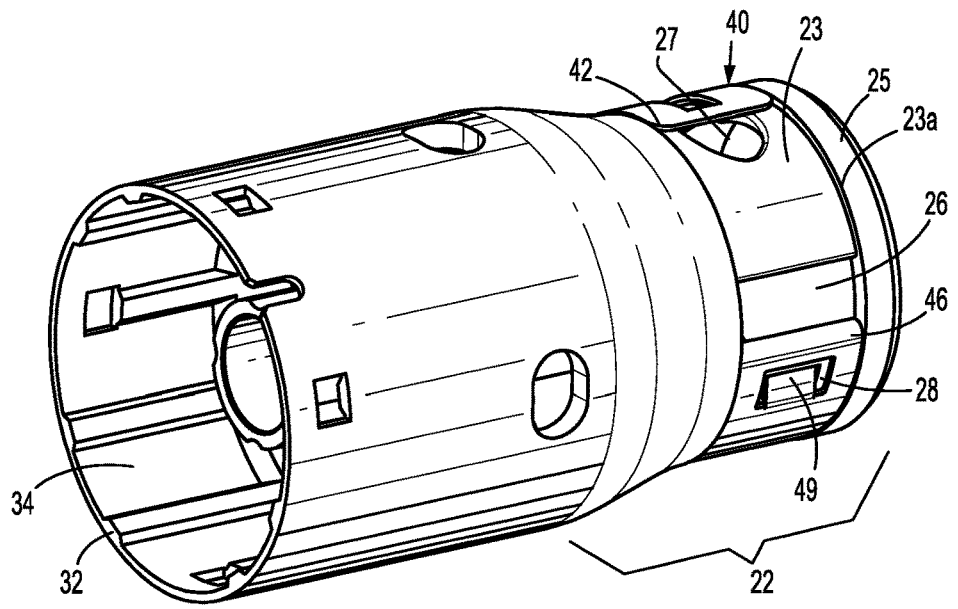
FIG. 6 is an enlarged perspective view of the loading unit of FIG. 2 with a staple cartridge removed from a shell assembly of the loading unit.

Referring to FIGS. 4-6, the shell assembly 20 includes a proximal end portion 22 that defines an opening 24 (FIG. 7) shaped to receive the distal end 110 (FIG. 2) of the adapter 100 and a distal end 32 that defines a receptacle 34 for selectively receiving the staple cartridge 12 (FIG. 2). In embodiments, the opening 24 and the receptacle 34 have a cylindrical shape. The proximal end portion 22 of the shell assembly 20 includes an annular surface 23 that defines an annular groove 23a. The annular groove 23a receives the attachment member or retention band 40 to releasably secure the shell assembly 20 to the adapter 100. The radial groove 23a may be sized to receive the retention band 40 such that the retention band 40 forms a continuous surface with an outer surface of the proximal end portion 22 of the shell assembly 20. The proximal end portion 22 includes a proximal ring 25 positioned at a proximal end of the annular surface 23 and defines a clip opening 26, an engagement window 27, and a tab opening 28 that extends through the annular surface 23. The engagement window 27 and the tab opening 28 are radially spaced apart from one another along the annular surface 23 with the clip opening 26 positioned therebetween.

Figure 7:
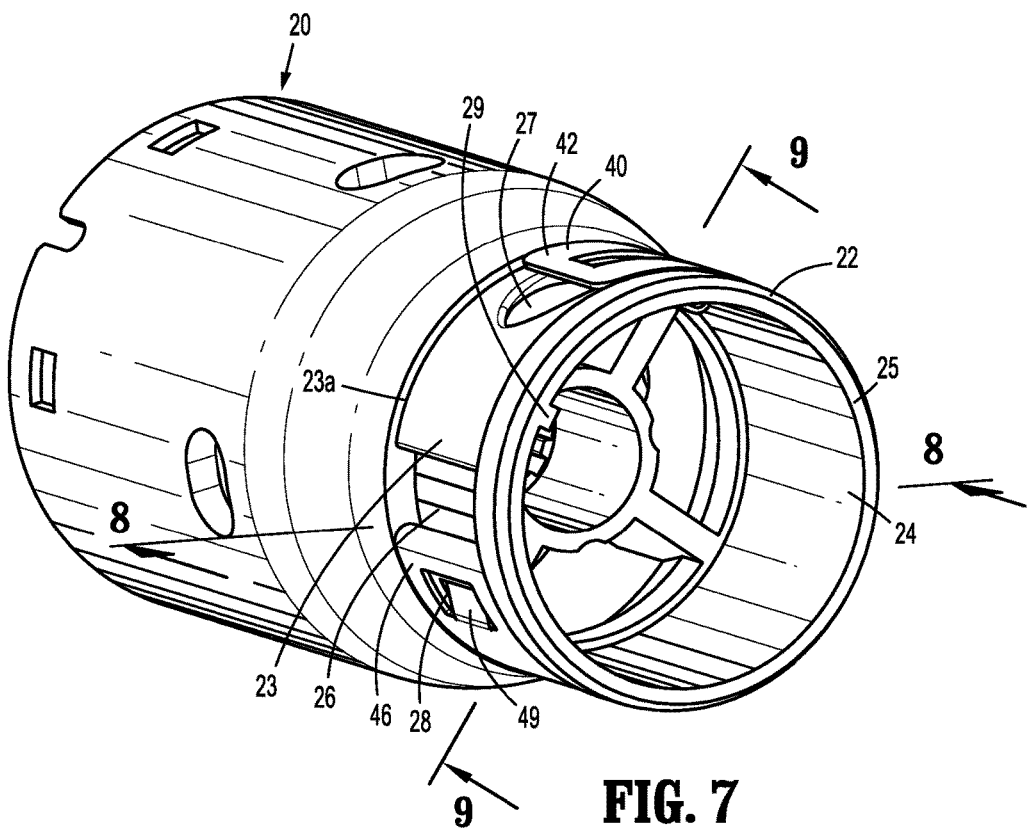
FIG. 7 is a rear perspective view of the loading unit of FIG. 4.
Figure 8:
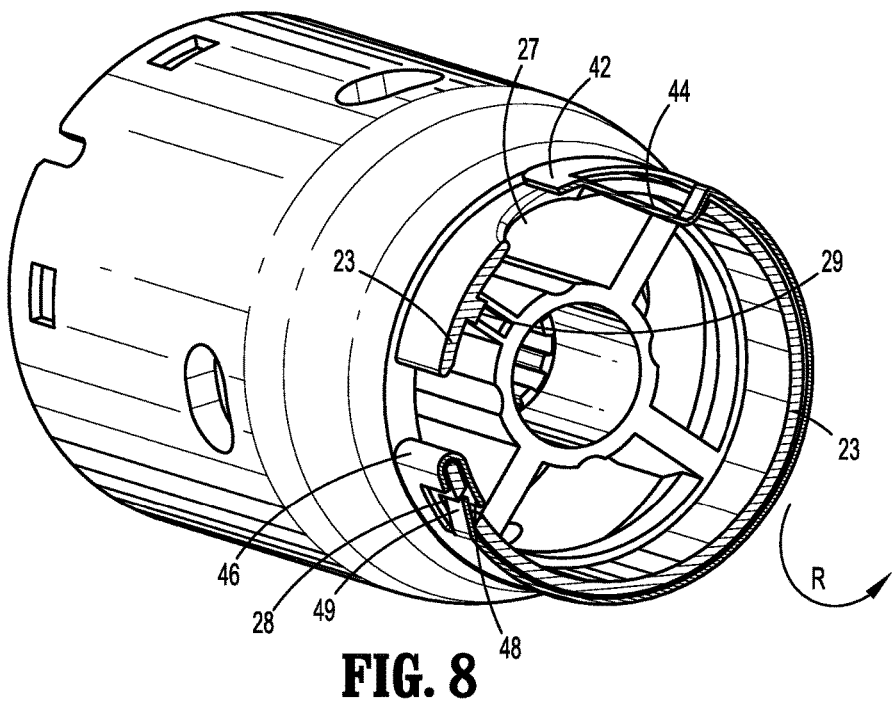
FIG. 8 is a cross-sectional view taken along the section line 8-8 of FIG. 7.

Referring briefly to FIGS. 7 and 8, the proximal end portion 22 of the shell assembly 20 includes a key 29 which protrudes from an inner surface of the proximal end portion 22 and extends towards a longitudinal axis of the shell assembly 20. In embodiments, the key 29 extends in a direction parallel to the longitudinal axis of the shell assembly 20 and is positioned between the engagement window 27 and the clip opening 26. It is contemplated that the key 29 may be positioned anywhere about the inner surface of the proximal end portion 22 of the shell assembly 20 and may extend proximally from a position within the annular surface 23 and onto the inner surface of the proximal ring 25 as shown in FIG. 7.

Referring again to FIGS. 4-6, the retention band 40 includes a body 45 having first and second ends 42, 46. The first end 42 includes a lock 44 that is sized to be received within the engagement window 27 of the shell assembly 20. The lock 44 includes a tapered portion 44a adjacent the first end 42 and a radial portion 44b adjacent the body 45. The second end 46 is bent backwards to form a clip 48. The second end 46 also includes an inwardly extending, resilient tab 49 which extends towards the clip 48. The clip 48 is sized to pass through the clip opening 26 formed in the proximal end portion 22 of the shell assembly 20 and to capture a portion of the annular surface 23 of the proximal end portion 22 between the clip 48 and the body 45 of the band 40. The tab 49 is sized to be received within the tab opening 28 defined in the annular surface 23 to secure the second end 46 of the retention band 40 to the shell assembly 20.

Referring also to FIGS. 7 and 8, the retention band 40 is attached to the shell assembly 20 by positioning the body 45 of the retention band 40 about the annular surface 23 of the proximal end portion 22 of the shell assembly 20 and inserting second end 46 of the retention band 40 into the clip opening 26 defined through the annular surface 23. The clip 48 is positioned such that a portion of the annular surface 23 is captured between the clip 48 and the body 45 of the retention band 40. The retention band 40 is rotated in a first direction as shown by Arrow R (FIG. 8) until the portion of the annular surface 23 abuts the second end 46 of the retention band 40 between the clip 49 and the body 45. As the portion of the annular surface 23 moves into abutment with the second end 46 of the retention band 40, the tab 48 snaps through the tab opening 28 to secure the second end 46 of the retention band 40 to the shell assembly 20. More specifically, as the retention band 40 is rotated in the first direction indicated by Arrow R, the tab 48 is urged away from the longitudinal axis of the shell assembly 20 by engagement with the annular surface 23 until the tab 48 passes over and snaps into the tab opening 28. When the tab 48 is positioned within the tab opening 28, the tab 48 prevents the retention band 40 from rotating in a second direction opposite the first direction via engagement of the tab 48 with the portion of the proximal end portion 22 of the shell assembly 20 captured between the clip 49 and the tab 48.

When the second end 46 of the retention band 40 is secured to the shell assembly 20, the body 45 of the retention band 40 is positioned within the groove 23a defining the annular surface 23 such that the body 45 is in contact with the annular surface 23. In this position, the lock 44 on the first end 42 of the retention band 40 passes through the engagement window 27. When the lock 44 is positioned within the engagement window 27, the radial portion 44b of the lock 44 engages a portion of the proximal end portion 22 defining the engagement window 27 to prevent the retention band 40 from rotating in the second direction. In embodiments, the body 45 of the retention band 40 is formed of a resilient material which is flexed outwardly when positioned about the proximal end portion 22 of the shell assembly 20. As such, the resilience of the body 45 urges the first and second ends 42, 46 of the retention band 40 towards one another. This biasing of the body 45 assists in securing the retention band 40 to the shell assembly 20.

Figure 9:
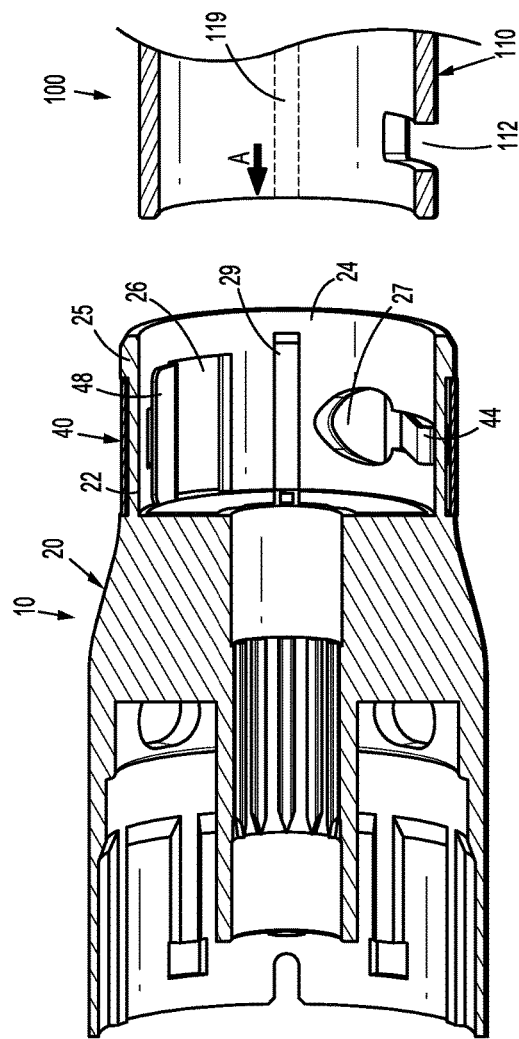
FIG. 9 is a side cross-sectional view taken along the section line 9-9 of FIG. 7 and a portion of the adapter of FIG. 2.

Referring to FIGS. 9-12, to secure the loading unit 10 to the distal end 110 of the adapter 100 or an elongated body of a manually actuated surgical instrument, the longitudinal axis of the shell assembly 20 is aligned with the longitudinal axis of the adapter 100 as shown in FIG. 9. In addition, the proximal end portion 22 of the shell assembly 20 is radially aligned with the distal end 110 of the adapter 100 such that the key 29 of the shell assembly 20 is aligned with the keyway 119 of the adapter 100. It will be appreciated that when the key 29 is aligned with the keyway 119, the attachment window 112 of the adapter 100 is aligned with the engagement window 27 of the shell assembly 20 (FIG. 9).

Figure 10:
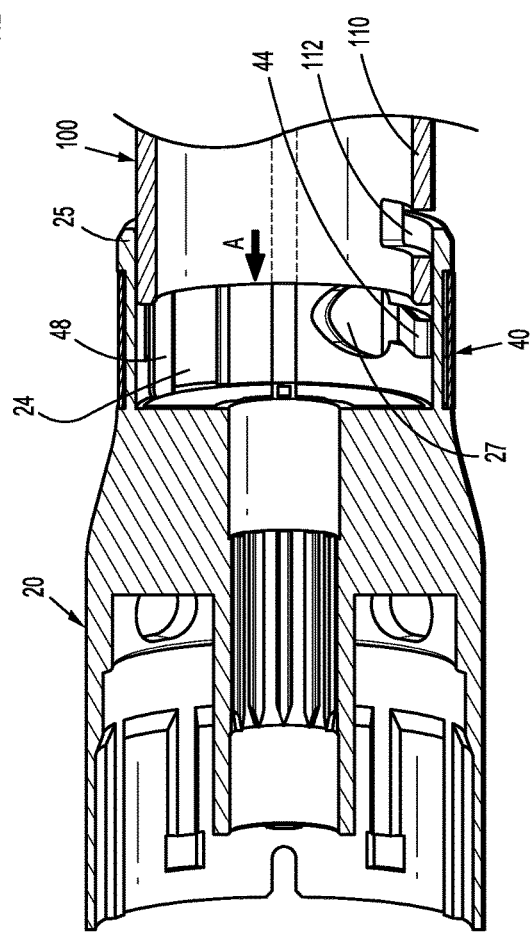
FIG. 10 is a side cross-sectional view of the loading unit and adapter of FIG. 9 with the distal end of the surgical instrument received in the proximal end of the loading unit.

With the key 29 aligned with the keyway 119, the distal end 110 of the adapter 100 is positioned within the opening 24 of the shell assembly 20 (FIG. 10). The adapter 100 is slid into the opening 24 of the shell assembly 20 until the distal end 110 of the adapter 100 is positioned adjacent the lock 44 of the retention band 40 that extends through the engagement window 27 of the shell assembly 20. The distal end 110 of the adapter 100 may be inserted into the cylindrical opening 24 until the distal end 110 abuts the lock 44 of the retention band 40 (FIG. 10).

With reference to FIG. 11, when the distal end 110 of the adapter 100 is adjacent or abutting the lock 44 of the retention band 40, the first end 42 of the retention band 40 is manually lifted in the direction indicated by Arrow B to move the first end 42 of the retention band 40 off the annular surface 23 of the shell assembly 20. When the first end 42 of the retention band 40 is lifted off the annular surface 23, the lock 44 is moved from within the engagement window 27 to permit the distal end 110 of the adapter 100 to slide into the shell assembly 20 to a position in which the attachment window 112 of the adapter 100 is longitudinally aligned with the engagement window 27 of the shell assembly 20 (FIG. 12). With the windows 27 and 112 aligned with each other, the first end 42 of the retention band 40 is released such that the retention band 40, which is in tension, clamps back onto the proximal end portion 22 of the shell assembly 20 such that the lock 44 extends through the engagement window 27 of the shell assembly 20 and the attachment window 112 of the adapter 100 to longitudinally fix the shell assembly 20 to the adapter 110. It will be appreciated that the resilience of the body 45 of the retention band 40 urges the lock 44 of the first end 42 through the windows 27 and 112 as represented by Arrow C (FIG. 12). When the lock 44 extends through the windows 27 and 112, the loading unit 10 is secured to the adapter 100.

With the loading unit secured to the adapter 100, the adapter 100 and loading unit 10 may be used to perform a surgical procedure. After surgical procedure is completed, the loading unit 10 is released from the adapter 100 by lifting the first end 42 to remove the lock 44 from the attachment window 112 of the adapter 100 and separating the loading unit 10 from the adapter 100. When the attachment window 112 is positioned distal to the engagement window 27 of the loading unit 10, the first end 42 may be released. With the loading unit 10 separated from the adapter 100, the adapter 100 may be sterilized for reuse in another surgical procedure or attached to a new loading unit for use again in the ongoing surgical procedure. In addition, the loading unit 10 may be sterilized for use in another surgical procedure or may be discarded.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A loading unit and retention band assembly comprising:
a shell having a proximal end portion defining an engagement window, the proximal end portion including an annular surface and defining a clip opening radially offset from the engagement window; and
a retention band disposed radially about the annular surface of the proximal end portion, the retention band including a resilient body having a first end and a second end, the first end including a resilient lock configured to extend through the engagement window of the proximal end portion of the shell, the resilient lock configured to releasably engage a surgical instrument to secure the shell to the surgical instrument, the resilient lock of the retention band extending through the engagement window towards a longitudinal axis of the shell, the second end of the retention band including a clip, the clip extending through the clip opening and configured to capture a portion of the proximal end portion of the shell between the clip and the resilient body of the retention band.

2. The assembly according to claim 1, wherein the shell includes a distal end portion configured to support a staple cartridge.

3. The assembly according to claim 1, wherein the annular surface defines an annular groove, the resilient body of the retention band being disposed within the annular groove.

4. The assembly according to claim 1, wherein the proximal end portion of the shell defines a tab opening, the clip opening being positioned between the engagement window and the tab opening, and wherein the retention band includes a tab adjacent the second end of the body, the tab extending from the resilient body towards the clip through the tab opening to fix the second end of the retention band relative to the proximal end portion of the shell.

5. The assembly according to claim 1, wherein the resilient body of the retention band is configured to urge the first and second ends towards one another.

6. A surgical instrument and loading unit assembly comprising:
a loading unit including a shell having a proximal end portion including an annular surface and defining an engagement window, the shell defining a longitudinal axis and the proximal end portion of the shell including a key protruding inward from the proximal end portion;
a surgical instrument having a distal end received within the proximal end portion of the shell, the distal end of the surgical instrument defining an attachment window and a keyway, the keyway receiving the key to radially fix the loading unit and the surgical instrument relative to one another; and
a retention band disposed radially about the annular surface of the proximal end portion, the retention band having a resilient body including first and second ends, the first end including a resilient lock extending through the engagement window of the proximal end portion of the shell, through the attachment window of the distal end of the surgical instrument, and engaged with the distal end of the surgical instrument to releasably couple the loading unit to the surgical instrument.

7. The assembly according to claim 6, wherein the key is positioned about the proximal end portion of the loading unit and the keyway is positioned about the distal end of the surgical instrument to radially align the engagement window of the loading unit with the attachment window of the surgical instrument.

8. A loading unit and retention band assembly comprising:
a shell having a proximal end portion defining an engagement window, the proximal end portion including an annular surface, the proximal end portion of the shell defining a clip opening radially offset from the engagement window, the proximal end portion of the shell defining a tab opening; and
a retention band disposed radially about the annular surface of the proximal end portion, the retention band including a resilient body having a first end and a second end, the first end including a resilient lock, the resilient lock of the retention band extending through the engagement window of the proximal end portion of the shell towards a longitudinal axis of the shell, the resilient lock being dimensioned to releasably engage a surgical instrument, the second end of the retention band including a clip, the clip extending through the clip opening and being configured to capture a portion of the proximal end portion of the shell between the clip and the resilient body of the retention band, the clip opening being positioned between the engagement window and the tab opening, and the retention band including a tab adjacent the second end of the body, the tab extending from the resilient body towards the clip through the tab opening to fix the second end of the retention band relative to the proximal end portion of the shell.

* * * * *